US012290157B2

(12) United States Patent
Kosecoff

(10) Patent No.: US 12,290,157 B2
(45) Date of Patent: May 6, 2025

(54) CARTRIDGE WITH DRY SHAMPOO FOR APPLICATOR DEVICE

(71) Applicant: L'Oreal, Paris (FR)

(72) Inventor: David B. Kosecoff, San Francisco, CA (US)

(73) Assignee: L'Oreal, Paris (FR)

( * ) Notice: Subject to any disclaimer, the term of this patent is extended or adjusted under 35 U.S.C. 154(b) by 713 days.

(21) Appl. No.: 17/025,608

(22) Filed: Sep. 18, 2020

(65) Prior Publication Data

US 2022/0087393 A1    Mar. 24, 2022

(51) Int. Cl.

| | |
|---|---|
| *A45D 24/28* | (2006.01) |
| *A45D 19/02* | (2006.01) |
| *A45D 24/32* | (2006.01) |
| *A46B 15/00* | (2006.01) |
| *A61K 8/02* | (2006.01) |
| *A61Q 5/02* | (2006.01) |

(52) U.S. Cl.
CPC .......... *A45D 24/28* (2013.01); *A45D 19/026* (2021.01); *A45D 24/32* (2013.01); *A46B 15/0004* (2013.01); *A46B 15/002* (2013.01); *A46B 15/0022* (2013.01); *A46B 15/0036* (2013.01); *A61K 8/022* (2013.01); *A61Q 5/02* (2013.01); *A45D 2200/057* (2013.01); *A46B 2200/104* (2013.01)

(58) Field of Classification Search
CPC ........ A45D 24/28; A45D 24/24; A45D 24/26; A45D 24/22; A45D 24/32; A45D 19/026; A46B 2200/104; A46B 15/004; A46B 11/0006; A46B 15/002

USPC .......................................................... 132/114
See application file for complete search history.

(56) References Cited

U.S. PATENT DOCUMENTS

| | | | | |
|---|---|---|---|---|
| 2,074,481 | A | | 3/1937 | Macmullen et al. |
| 3,457,928 | A | * | 7/1969 | Kurshenoff ............ A45D 24/26 401/28 |
| 6,161,729 | A | * | 12/2000 | Gentile .............. B65D 81/3288 222/129 |
| 2005/0000535 | A1 | * | 1/2005 | Kim ....................... A45D 24/22 132/114 |
| 2006/0283474 | A1 | * | 12/2006 | Anderson ............ A45D 19/026 132/126 |

(Continued)

FOREIGN PATENT DOCUMENTS

| | | | | |
|---|---|---|---|---|
| CN | 105639986 | * | 6/2016 | ............ A45D 20/52 |
| DE | 102016209059 | * | 11/2017 | |

(Continued)

OTHER PUBLICATIONS

JP S62187843, Nov. 30, 1987 [retrieved on Jan. 3, 2025]. Translation retrieved from: Google Patents (Year: 1987).*

(Continued)

*Primary Examiner* — Cris L. Rodriguez
*Assistant Examiner* — Courtney N Huynh
(74) *Attorney, Agent, or Firm* — Christensen O'Connor Johnson Kindness PLLC

(57) ABSTRACT

A device for treating hair or scalp, the device comprises a dispenser connected to a cartridge, wherein the cartridge comprises a formulation; a plurality of tips, wherein the tips have at least one opening to dispense the formulation; and a controller that controls the amount of formulation that is dispensed from the tips.

15 Claims, 13 Drawing Sheets

(56) References Cited

U.S. PATENT DOCUMENTS

| | | | |
|---|---|---|---|
| 2008/0007273 A1* | 1/2008 | Sherman | G01N 22/04 |
| | | | 324/640 |
| 2011/0308034 A1 | 12/2011 | Powers et al. | |
| 2015/0189980 A1 | 7/2015 | Hwang et al. | |
| 2016/0286929 A1* | 10/2016 | Delabastide | A45D 24/26 |
| 2019/0209078 A1 | 7/2019 | Charraud et al. | |
| 2020/0196937 A1 | 6/2020 | Gopalan | |

FOREIGN PATENT DOCUMENTS

| | | | | |
|---|---|---|---|---|
| DE | 102016209059 A1 | * | 11/2017 | |
| EP | 0150871 | * | 8/1985 | A45D 24/10 |
| JP | S62187843 | * | 5/1986 | |
| JP | S61188503 U | | 11/1986 | |
| JP | S62187843 U | * | 11/1987 | |
| JP | 2001275737 A | | 10/2001 | |
| JP | 2007526804 A | | 9/2007 | |
| JP | 2010131260 A | | 6/2010 | |
| KR | 20070074211 | * | 1/2006 | |
| KR | 101782267 | * | 9/2017 | A45D 24/28 |
| KR | 101 989 070 B1 | | 6/2019 | |
| KR | 101989070 | * | 6/2019 | A45D 24/22 |
| WO | WO-0027240 A1 | * | 5/2000 | A45D 19/02 |
| WO | WO 00127240 | * | 5/2000 | |
| WO | WO 2004010818 | * | 2/2004 | |
| WO | WO-2004010818 A1 | * | 2/2004 | A45D 19/02 |
| WO | 2009/096289 A1 | | 8/2009 | |
| WO | 2012/026277 A1 | | 3/2012 | |
| WO | 2018/164905 A1 | | 9/2018 | |
| WO | 2018/224639 A1 | | 12/2018 | |
| WO | 2019136232 A1 | | 7/2019 | |

OTHER PUBLICATIONS

CN 105639986 (Chen Ping) Portable electric smart hair washing comb, Jun. 8, 2016 [retrieved on Jan. 3, 2025]. Translation retrieved from: Google Patents (Year: 2016).*
DE 102016209059 (Michael Schlör, Armin Faul) Device for hair and/or scalp care, Nov. 30, 2017 [retrieved on Jan. 3, 2025]. Translation retrieved from: Google Patents (Year: 2017).*
KR 101782267 (Jang Gyeong Ok) (Gimcheon Univ) Treatment for scalp hair comb sprayer functions provided, 2017-09-28 [ retrieved on Jan. 3, 2025]. Translation retrieved from: Google Patents (Year: 2017).*
KR 101989070 (Lee So Hyeon). Hair brush for scalp management, Jun. 13, 2019 [retrieved on Jan. 3, 2025]. Translation retrieved from: Google Patents (Year: 2019).*
International Preliminary Report on Patentability, mailed Mar. 30, 2023, in corresponding International Patent Application No. PCT/US2021/050966, 16 pages.
Invitation to Pay Additional Fees and Annex, Communication Relating to the Results of the Partial International Search mailed Nov. 15, 2021, in corresponding PCT Application No. PCT/US2021/050966, filed Sep. 17, 2021, 17 pages.
Notification of Reasons for Refusal for JP App. No. 2023-517960 dated Dec. 14, 2023.
1 Communication for EP App. No. 21782623.9 filed on Sep. 17, 2021, dated Mar. 5, 2024. 6 pages.
CN Office Action dated May 6, 2024 for CN Patent Application No. 2021800778622. 7 pages.
Office Action for EP Pat. App. No. 21782623.9, dated Sep. 10, 2024. 6 pages.
Chinese Office Action mailed Oct. 31, 2024, issued in related Chinese Application No. 202180077862.2 filed Sep. 17, 2021, 5 pages.
Office Action dated Jul. 26, 2024, issued for Korean Pat. App. No. 10-2023-7012473 filed Sep. 17, 2021.

* cited by examiner

CARTRIDGE WITH DRY SHAMPOO FOR APPLICATOR DEVICE

SUMMARY

Typically, dry shampoo is self-applied to a head of hair using an aerosol can. The spray creates a particle cloud that can get on unintended targets, such as the users face and skin and clothes and can be inhaled by the user. The aerosol itself can be bad for the environment. Furthermore, the application method and form factor of aerosol can-based dry shampoos limit the use mainly for home bathrooms. Aerosol cans are not sized for small carry bags and the spray cloud makes aerosolized sprays inappropriate to use around other individuals.

In one embodiment, an advantage of this disclosure is to provide a device for dispensing dry shampoo in a cleaner and more accessible form.

In one embodiment, a cartridge containing dry shampoo solution is embedded in a applicator device. When activated via an on-button the dry shampoo solution is dispensed in measured amounts via a pump into a series of tips or teeth with small openings in them. As the user combs or brushes their hair, the solution glides onto and into the hair.

In one embodiment, the device releases hair and scalp product as a vapor cloud (mist) through ultrasound. This has the advantage of gentle dispersion of the product to reduce the amount of waste and improves control of coverage. This solution contrasts with an aerosol spray can that sprays more than is needed and produces a large cloud that covers an area well outside the user's head.

In one embodiment, a multi-use device incorporates novel brush or comb tips for dispensing.

In one embodiment, each tip is constructed as a joining of a half-cylinder positive conductor and half-cylinder negative conductor, separated by a non-conductive gasket (insulator).

In one embodiment, each brush (or comb) tip is a cylindrical chamber split lengthwise into two or more chambers electrically insulated from each other, or two or more coaxial cylinders electrically insulated from each other.

In one embodiment, a tip has a positive terminal that can be used to provide micro-currents to the scalp, where the scalp acts as ground (GND) path.

In one embodiment, the brush (or comb) tip can provide micro-currents to the scalp, where the scalp acts as a conductive path between a positive terminal and a negative terminal of different tips.

In one embodiment, micro-currents can be administered between multiple tips, where one tip acts at the positive source terminal and the other acts as a GND terminal.

In one embodiment, impedance can be measured between the positive and negative terminals to determine scalp moisture level.

In one embodiment, impedance can be measured between multiple tips to determine scalp moisture level across wider regions.

In one embodiment, impedance can be measured between the positive terminal or negative terminal and scalp (via return path to handle) to determine if tip is in contact with scalp (skin). This is useful if the application requires scalp contact; for instance, in a formula treatment and vacuuming system, where the scalp is the treatment target and the vacuum is at risk of vacuuming hair if it's not operating directly on the scalp.

In one embodiment, a light-emitting diode (LED) can be placed at the end of the tip and powered by the two terminals.

In one embodiment, depending on the power of the LED, thermal dissipation can be absorbed (heatsinked) by the conductive material.

In one embodiment, LEDs are placed at the far end of the tip. In this configuration, an LED can deliver more energy to the scalp compared to being placed at the base of the tip or delivered through a long fiber-optic path.

In one embodiment, the LED can be used for treatment, curing formula, or indicating device status (i.e., operational mode or charging status).

In one embodiment, a series of laser-cut holes (perforations) along the length of the tips can be used to deliver formula to the scalp and hair.

In one embodiment, individual openings only at the very end of the tip can be used if only the scalp is targeted.

In one embodiment, The functions of the tips and their split conduction halves can be controlled by a microprocessor circuit within the primary body of the brush or comb device.

In one embodiment, the brush or comb tip is not conductive, and the multi-cylinder construction can be useful if the application involves mixing formulas or dispensing formula and vacuuming onto a small, controlled target area on the scalp.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

This disclosure relates to a device for cleansing hair that can be used with dry shampoo formulations. In one embodiment, the device uses a brush- or comb-like architecture that relies on a combination of mechanical and chemical action to deposit desired formulations for cleansing, removing the formulations with unwanted particulates, and further provides additional cosmetic or health attributes. The comb-like action provides a familiar gesture easy to incorporate into current beauty and haircare routines. Further, the device can include hollow conductive tips arranged in a brush or comb configuration. The tips being conductive allows several options, for example, the conductive tips can be used with a micro-current generator, or the conductive tips can be used with an electrostatic charger to charge the scalp or hair with positive or negative charges that will attract hair formulations to the charged areas.

In one embodiment, the device is provided with tines or tips utilizing a hollow construction that allows more precise delivery of the formulation. In an embodiment, the tines and tips can be used to provide micro-currents or electrostatic charges to the scalp and hair. In an embodiment, the tips can be used as a contact sensor. In an embodiment, the tips can be used to measure impedance to determine moisture content.

In one embodiment, the device 100 is shaped in the style of well-recognized familiar hair appliances to inspire trust and confidence in the device leading to intuitive use and gestures when using the device.

Referring to FIGS. 1 to 5, in one embodiment, the device 100 includes a handle 104 connected to a substantially cylindrical section 138. The handle 104 is connected to the device 100 at an obtuse angle with respect to the front end of the device 100. The handle 104 helps balance the device weight for more comfortable use and easier control. The control buttons can also be located on the handle.

Figure 3:
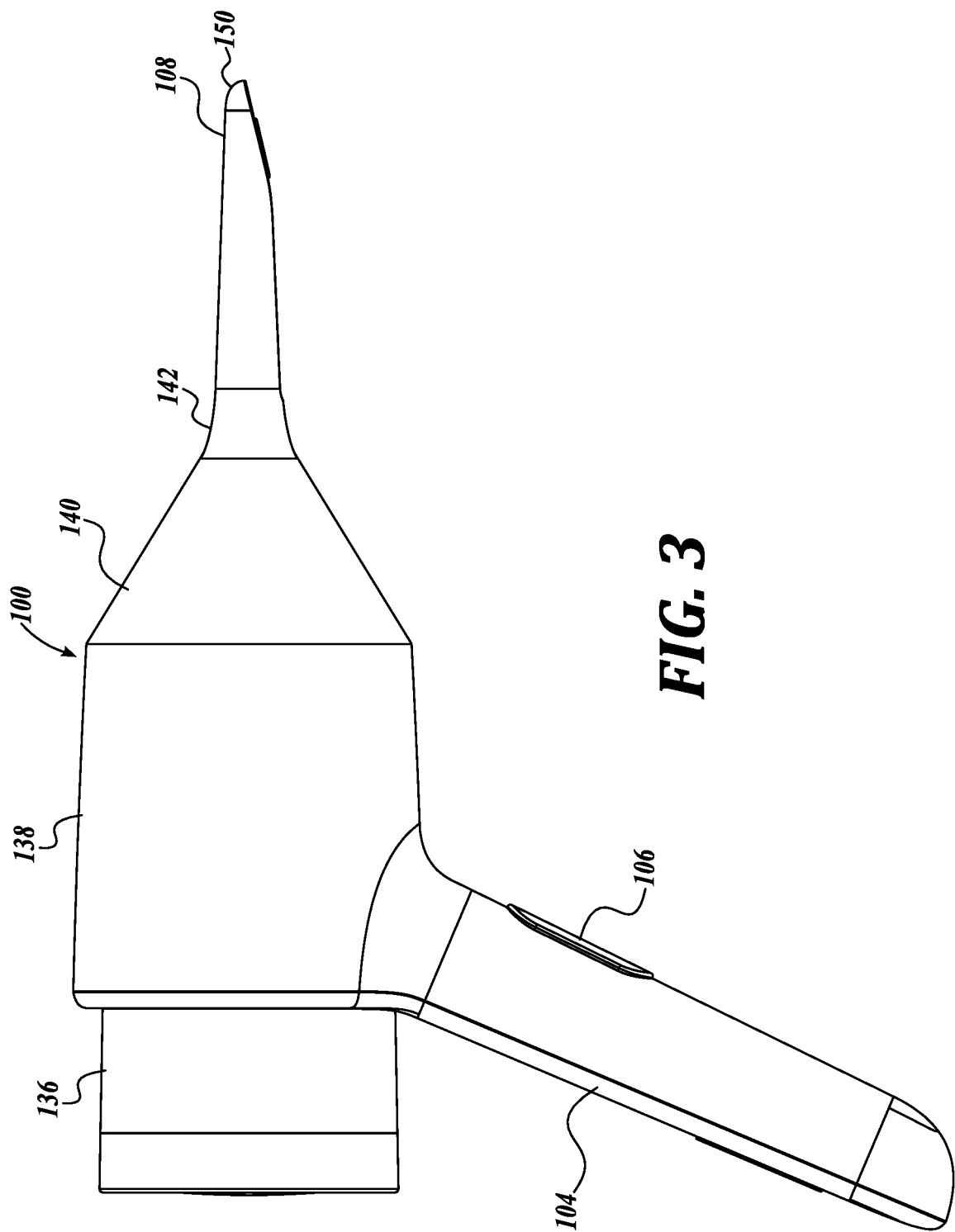
FIG. 3 is a diagrammatical illustration of a side view of the hair and scalp treatment device of FIG. 1.

Referring to FIG. 3, at the back side, the device 100 can include a smaller diameter cylindrical shaped housing 136 that accepts a removable cartridge 102 containing a hair or scalp treatment formulation. The cartridge 102 can be configured to be a re-fillable cartridge or a disposable cartridge. In one embodiment, the device 100 can be configured to hold more than one cartridges 102, wherein each cartridge can be filled with a different formulation for a different treatment. Alternatively, some applications may use two or more different formulations that require applying both formulations to achieve the intended affect.

Forward from the rear housing 136, the device 100 exterior shape increases step-wise to a larger outer diameter portion 138 compared to the housing 136 diameter. In one embodiment, the device 100 includes a body structure that has a substantially cylindrical or minimally tapered conical portion 138 from the back end to about the middle of the device length. In one embodiment, the handle 104 connects to the back side of portion 138. Then, proximally from the cylindrical or minimally conical portion 138, the device 100 takes on a more pronounced conical or decreasing elliptical shape 140 in the top to bottom plane (i.e., viewed from left or right side), from about the middle of the device 100 to about a third or fourth of the device length. However, in the side-to-side plane (i.e., viewed from top or bottom) the device 100 does not taper as much so as to be able to accommodate three tines in the side-to-side plane. As described herein, the tines 150 can be replaced with tips arranged in either a brush or comb configuration.

Then, distally from the smaller end of the conical or elliptical shape 140, the device 100 has a transition portion 142 that forms one or more dispensing tines 108 at the front end, so that each tine 108 is separate from the other tines. Although tines 108 are illustrated in connection with a hair or scalp treatment system, the device 100 can be configured as a brush or comb.

Figure 2:
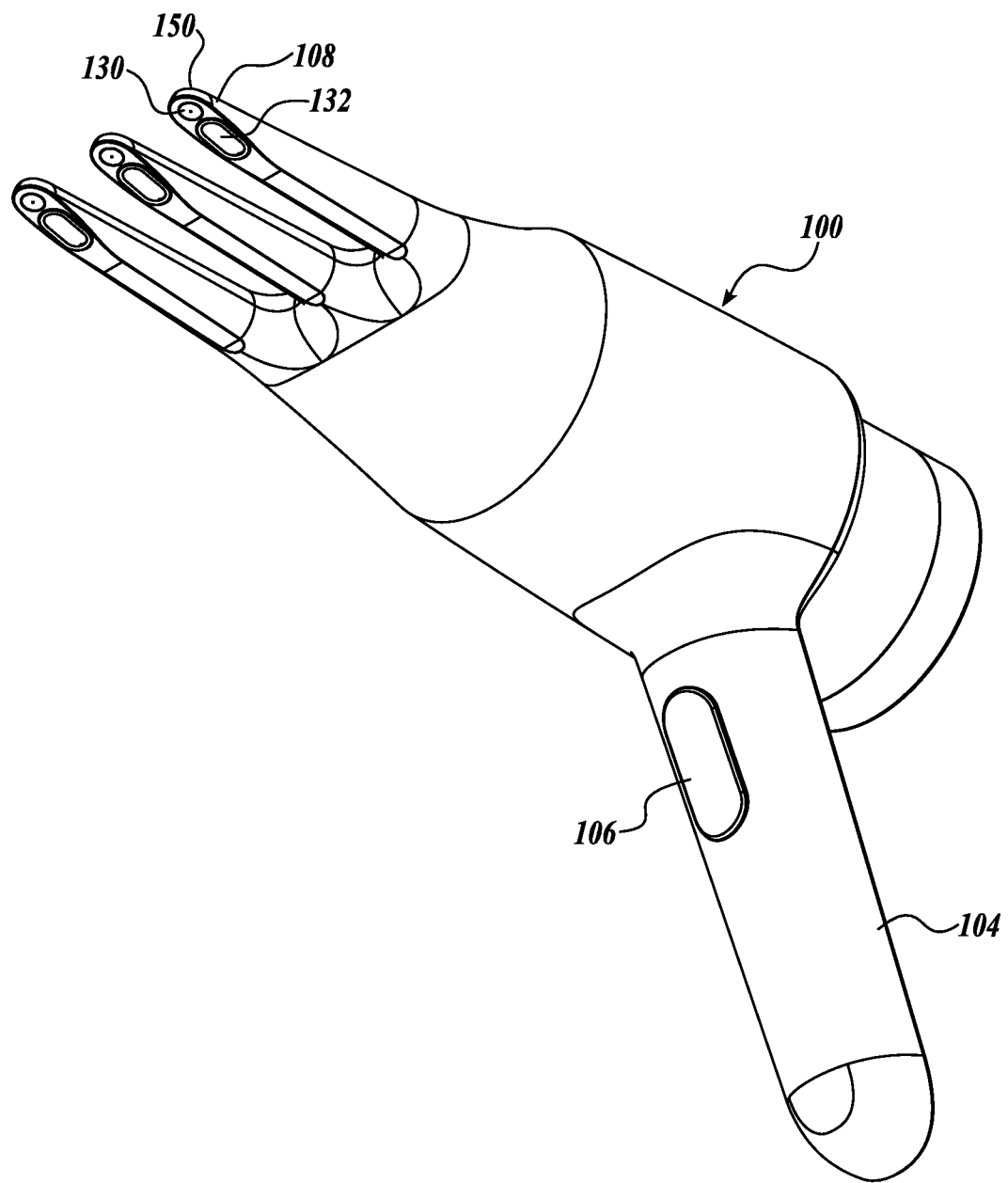
FIG. 2 is a diagrammatical illustration of the hair and scalp treatment device of FIG. 1.
Figure 5:
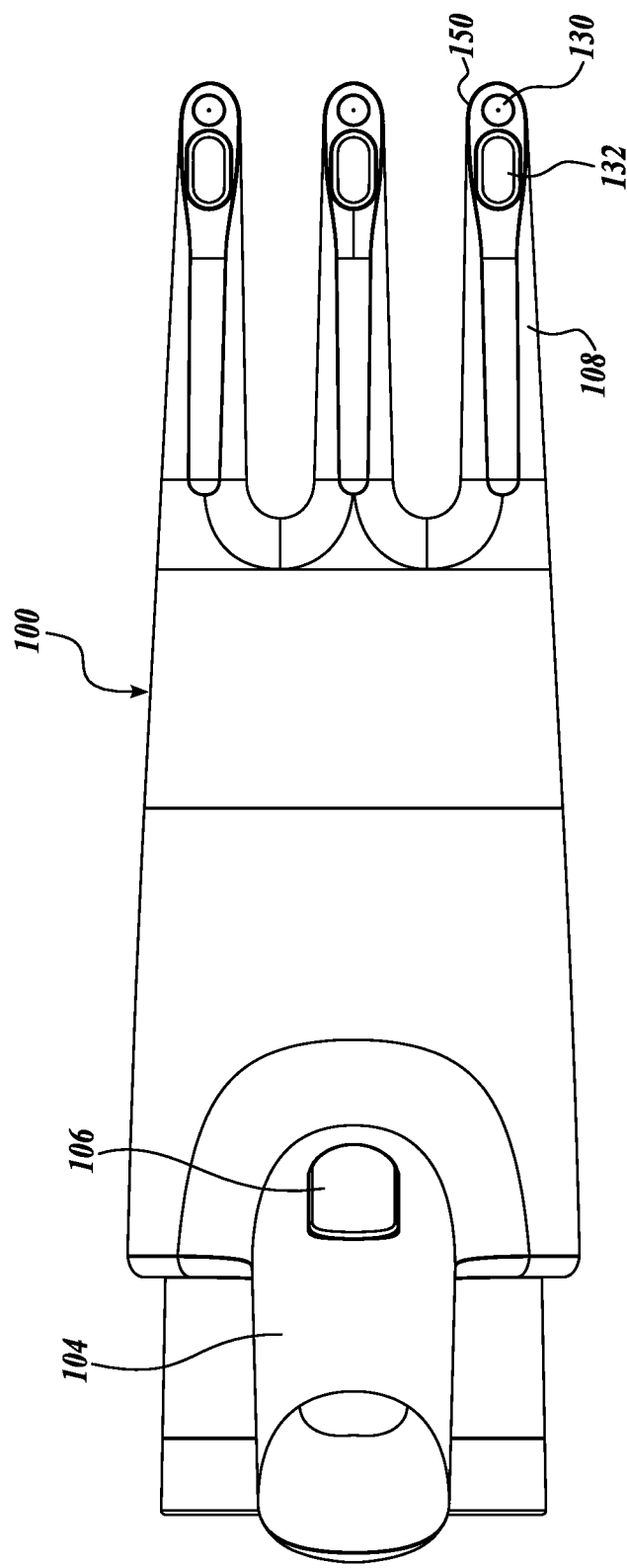
FIG. 5 is a diagrammatical illustration of a bottom view of the hair and scalp treatment device of FIG. 1.

Referring to FIGS. 2 and 5, each tine 108 has a gradually decreasing conical shape from the initial connection at the transition portion 142 section to the end of the tine 108 in both the side to side plane and the top to bottom plane.

In FIG. 5, the tines 108 are shown having a rounded tip when viewed from the bottom (or top) plane. However, in FIG. 3, the tines 108 are shown to have a flat area or chamfer at the bottom of the tine 108 at the front end when viewed from the side plane, resulting in a truncated rounded shape. The rounded tips of the tines 108 can part the hair for better access to the scalp and hair roots. The rounded tines 108 include "agitation bumps" and the chamfered angle for cleansing and massaging action.

In FIG. 5, the chamfered section of the tines 108 has openings 130 for dispensing one or more formulations. In one embodiment, openings 130 can be static, meaning the spray or dispensing direction is set and cannot be adjusted. In one embodiment, the openings 130 can be directional, meaning the spray or dispensing direction can be controlled. For example, the openings 130 can be provided on a swivel ball that is controlled through micro-actuators. In one embodiment, multiple openings can be provided, wherein each opening is oriented in a different direction, and the formulation is dispensed from the selected opening in the preferred orientation.

In one embodiment, the formulation can be dispensed as a liquid. In one embodiment, the formulation can be atomized and dispensed as a mist. Additionally, the chamfered section of tines 108 has openings 132 that lead to a vacuum system for collecting the used formulation with any debris or oils removed from the hair.

In the illustrated embodiment, each tine 108 is shown having openings 130 for dispensing and openings 132 for vacuuming. However, in one embodiment, there can be dedicated tines that only have openings for dispensing formulation and dedicated tines that only have openings used for vacuum. In one embodiment, there can be multiple openings on each tine 108 to provide for dispensing different formulations from the same tine. This can be advantageous where two formulations work together to achieve the intended affect. In one embodiment, each opening can be dedicated to a different formulation. In one embodiment, the device 100 is provided with three tines 108 for even cleansing coverage. The angle of the handle 104 and the tine 108 length allows users to reach all areas of the scalp and hair.

In one embodiment, the device 100 includes an electrostatic treatment system. In one embodiment, the purpose of the electrostatic system is to charge a portion of the scalp or hair or both by induction or contact. In one embodiment, an electrode 150 is placed at the tips of the tines 108. The electrode 150 can also electrostatically charge the hair formulation droplets as they are dispensed from the openings 130. The charged hair formulation will then become attracted or repelled, according to the particular charges produced, to the target areas of the scalp or the hair. The electrode 150 is electrically connected to an electrostatic charger. In one embodiment, the electrode 150 may be surrounded by electrically insulating material.

Figure 6:
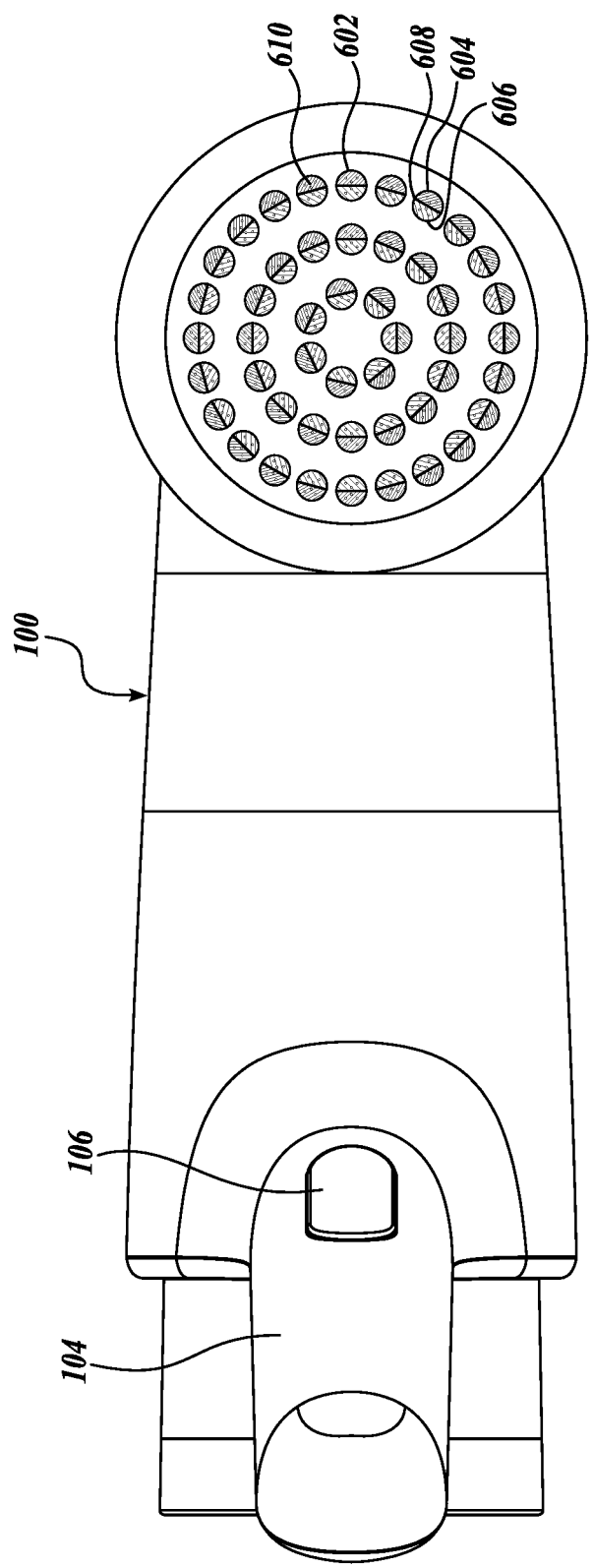
FIG. 6 is a diagrammatical illustration of a bottom view of a hair and scalp treatment device having tips arranged in a circular pattern utilizing half-cylinder construction (brush embodiment)
Figure 7:
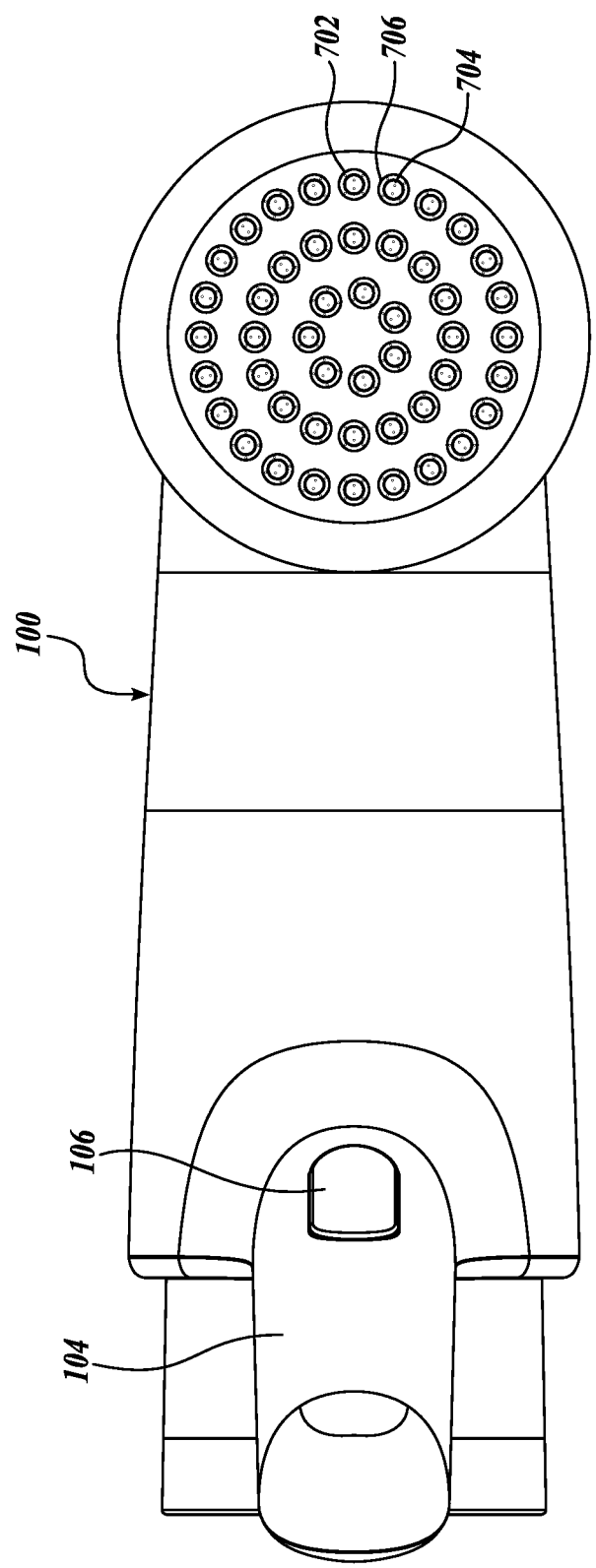
FIG. 7 is a diagrammatical illustration of a bottom view of a hair and scalp treatment device having tips arranged in a circular pattern utilizing cylinder within cylinder construction (brush embodiment)

In FIGS. 6 and 7, an embodiment of the device 100 is illustrated with a brush having tips 602, 702 instead of the tines of FIGS. 1 to 5. In one embodiment, the tips 602, 702 are arranged in concentric circles on the brush. In one embodiment, tips 602 and 702 can perform the functions of the tines 108 and also have added functionality. In an embodiment, the brush tips 602, 702 are configured to be able to dispense two different formulations from the tips 602 and 702. In an embodiment, tips 602 and 702 have hollow chambers that extend the entire length of the tips. Tips 602 and 702 are at least one diameter in length. However, tips 602 and 702 can be constructed to be several diameters in length, so the width to length ratio can vary from 1 to 1 to 1 to 20 or more. The tips 602 and 702 can be flexible or non-flexible. The segregated chambers allow one or more formulations to be delivered through each chamber without mixing. The formulations can be segregated within the respective chambers until the time the formulations exit the chambers. The dispensing of formulations can be accomplished by constructing each of the chambers with openings along the length or only at the ends or both along the length and ends of the chambers.

In an embodiment, chambers are depicted as half-cylinders and full cylinders, but the chambers may take on any cross-sectional shape. Additionally, in an embodiment, the tips 602, 702 and the first and second hollow chambers forming them can be electrically conductive so as to be configured as a positive and negative terminal to further provide micro-currents or electrostatic charging treatments to the scalp and hair. Further, conductive tips 602, 702 have other uses when the first and second hollow chambers are connected to a positive and negative terminal of a power supply or the first and second hollow chambers are connected to a positive and negative sensing terminal.

In one embodiment, the brush and comb tips 602, 702 are not conductive, and the multi-cylinder construction can be useful if the application involves mixing formulas or dispensing formula and vacuuming onto a small, controlled target area on the scalp.

Figure 9:
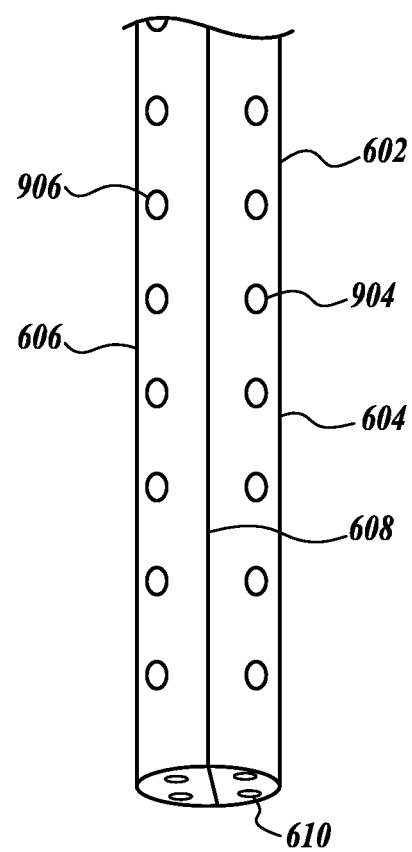
FIG. 9 is a diagrammatical illustration of a tip of half cylinder construction for the brush and comb embodiments.

Referring to FIG. 6, in one embodiment, each tip 602 is constructed as joining a first hollow half cylinder 604 to a second hollow half cylinder 606 along the length direction. The first 604 and second 606 half cylinders are separated by an insulator 608. FIG. 9 is an enlarged illustration showing the tips 602. Here, although the tip 602 is in the shape of a "cylinder," according to this disclosure a tip can have any cross-sectional shape, including oblong, rectangular, square, or any other polygon.

In one embodiment, the first hollow half cylinder 604 and the second 606 hollow half cylinder are made from a conductive material such as metal. In one embodiment, one of the first 604 or second 606 half cylinder will be designated a positive conductor terminal and the other half cylinder will be designated a negative conductor terminal.

In one embodiment, the first 604 and second 606 hollow chambers are made from or could be embedded with a shape memory or piezoelectric material that can be actuated by an electric current to control a direction of movement of the tips 602. In one embodiment, the chambers in a dual-chamber construction could be made of or embed a shape memory or piezoelectric materials that actuate in opposing directions from one another, allowing for plus and/or minus actuation about a center position depending on which chamber is activated. These materials can exist as polymers, ceramics, and alloys, for example. In one embodiment, the shape memory and piezoelectric materials can be fabricated as coils, and do not necessarily have to be hollow chambers. Coils are effective for actuating the tips vertically along the Z axis (i.e., in the axial direction of the coil). Electrical actuation of the shape memory and piezoelectric materials is via an AC or DC power source having a positive and negative terminal connected to the shape memory or piezoelectric material.

In one embodiment, the end of the tips 602 include a perforated disk having small openings 610 in both of the first 604 and second 606 half cylinders. In an embodiment, instead of a disk, the half cylinders 604 and 606 can be completely open at the end. Either construction allows dispensing formulation from the ends or along the length of the tips 602 or both along the length and ends of the tips.

Figure 10:
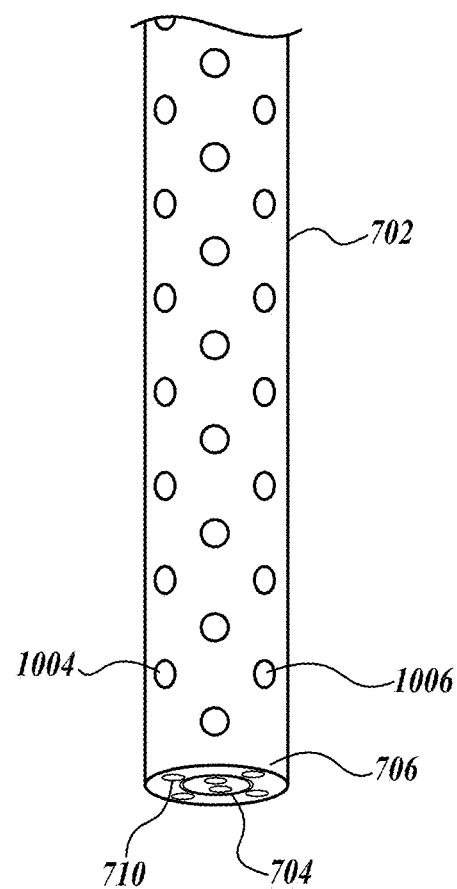
FIG. 10 is a diagrammatical illustration of a tip of cylinder within cylinder construction for the brush and comb embodiments.

Referring to FIG. 7, in one embodiment, the tip 702 is constructed by inserting a first hollow small diameter cylinder 704 into a second hollow larger diameter cylinder 706. FIG. 10 is an enlarged illustration showing the tips 702.

In one embodiment, the first cylinder 704 is coaxial with the second cylinder 706. The first cylinder 704 may be called the inner cylinder and the second cylinder 706 may be called the outer cylinder. Here, although the tip 702 is in the shape of a "cylinder," according to this disclosure a tip can have any cross-sectional shape, including oblong, rectangular, square, or any other polygon.

In one embodiment, the first cylinder 704 and the second 706 cylinder are made from a conductive material such as metal. In one embodiment, the exterior of the first smaller cylinder 704 can be coated with an insulator. An insulator is optional if the first 704 and second 706 cylinders cannot be electrically isolated from each other. In one embodiment, one of the first 704 or second 706 cylinders will be designated a positive conductor terminal and the other cylinder will be designated a negative conductor terminal.

In one embodiment, the first 704 and second 706 hollow chambers are made from or could be embedded with a shape memory or piezoelectric material that can be actuated by an electric current to control a direction of movement of the tips 702. In one embodiment, the chambers in a dual-chamber construction could be made of or embed a shape memory or piezoelectric materials that actuate in opposing directions from one another, allowing for plus and/or minus actuation about a center position depending on which chamber is activated. These materials can exist as polymers, ceramics, and alloys, for example. In one embodiment, the shape memory and piezoelectric materials can be fabricated as coils, and do not necessarily have to be hollow chambers. Coils are effective for actuating the tips vertically along the Z axis (i.e., in the axial direction of the coil). Electrical actuation of the shape memory and piezoelectric materials is via an AC or DC power source having a positive and negative terminal connected to the shape memory or piezoelectric material.

In one embodiment, the end of the tips 702 include a perforated disk having small openings 710 in both of the first 706 and second 706 cylinders. In an embodiment, instead of a disk, the inner and outer cylinders 704 and 706 can be completely open at the end. Either construction allows dispensing formulation from the ends or along the length of the tips 702 or both along the length and ends of the tips.

Figure 8:
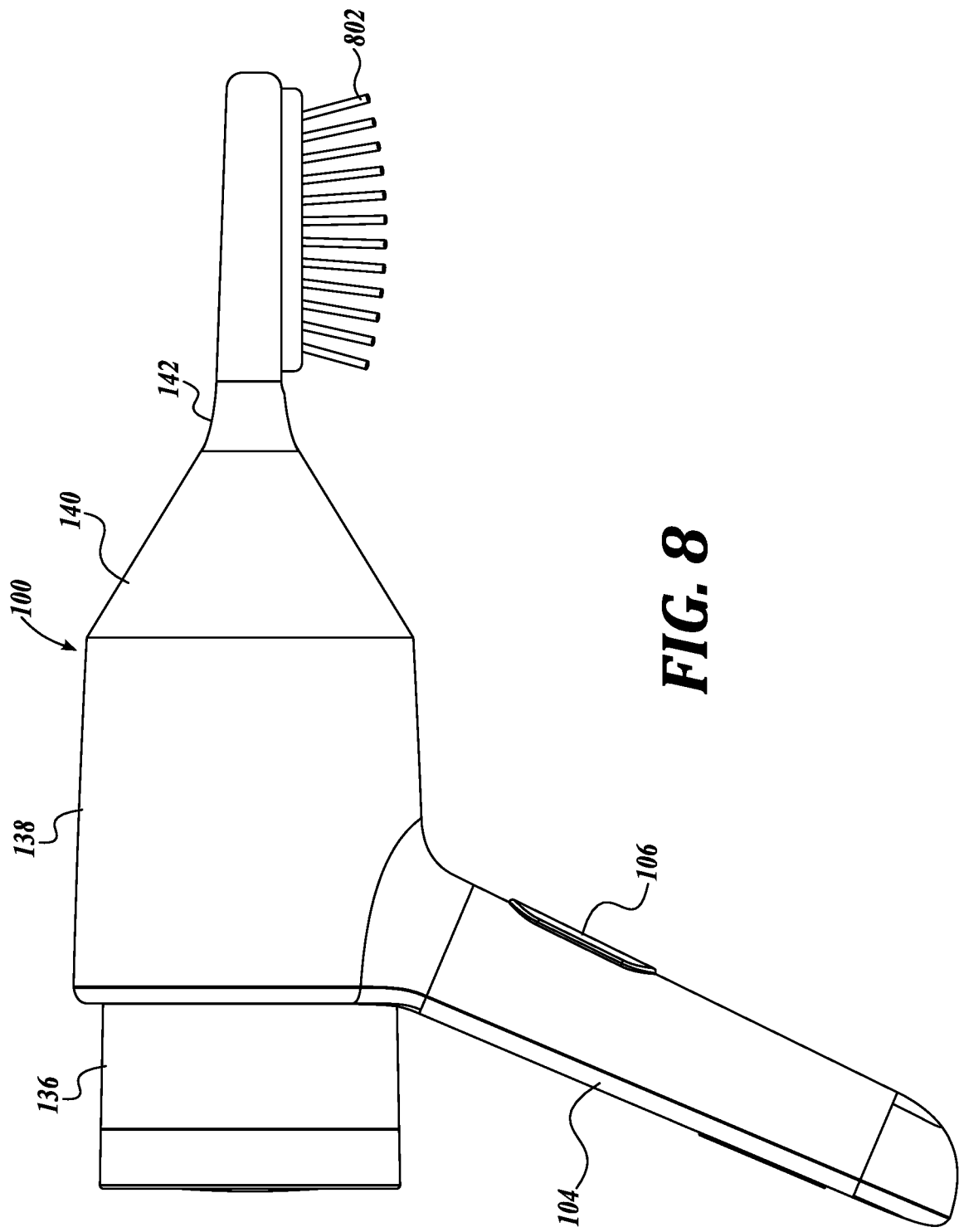
FIG. 8 is a diagrammatical illustration of a side view of a hair and scalp treatment device having tips arranged in a single row (comb embodiment)

Referring to FIG. 8, an embodiment of the device 100 is illustrated having the tips 802 arranged in a comb configuration. In one embodiment, tips 802 for the comb configuration are similar in materials and construction as compared to the tips 602, 702 illustrated in FIGS. 6, 7, 9, and 10, however, the difference being comb tips 802 can be arranged in a single row.

FIGS. 9 and 10 further illustrate that tips 602 and 702 can have openings on the exterior circumference as wells as at the ends. In FIG. 9, the hollow half cylinder 604 has first openings 904 along a length of the exterior, and the hollow half cylinder 606 has second openings 906 along a length of the exterior. In this way, two different formulations can be delivered from tips 602 via the half cylinder 604 and the half cylinder 606.

In FIG. 10, the inner cylinder 704 has first openings 1004 that appear on the exterior of outer cylinder 706; however, openings 1004 can be connected passing through the outer cylinder 706, so that openings are closed off to the outer cylinder 706, for example, by tubes that lead to the inner cylinder 704. The outer cylinder 706 has second openings 1006 along a length of the exterior, wherein openings 1006 only connect to the interior of the outer cylinder 706. In an embodiment, the inner cylinder 704 and outer cylinder 706 are not coaxial with each other, but, the inner cylinder 704 may be placed against the inner wall of the outer cylinder 706, thus, the openings from the inner cylinder 704 may only need to traverse the wall of the outer cylinder 706, thus, avoiding the need to connect openings via tubes. An insulator may need to be interposed between the inner 704 and outer 706 cylinders for electrical isolation. In either construction, two different formulations can be delivered from tips 702 via the inner 704 and outer cylinder 706.

In one embodiment, the openings can be made by laser-cut holes (perforations) along the length of tip can be used to deliver formula to the scalp and hair.

In one embodiment, tips 602 and 702 can omit openings along the length of the tips, and the tips 602, 702 are provided with openings only at the very ends so as to use the tips 602, 702 for treatment of the scalp.

In one embodiment, the tips 602 and 702 being made from conductive materials allows one of the cylinders 604 or 606 and 704 or 706 of each of the tips 602 and 702 to act as a positive terminal and the other to act as a negative terminal for the conduction of electrical charges.

Figure 11:
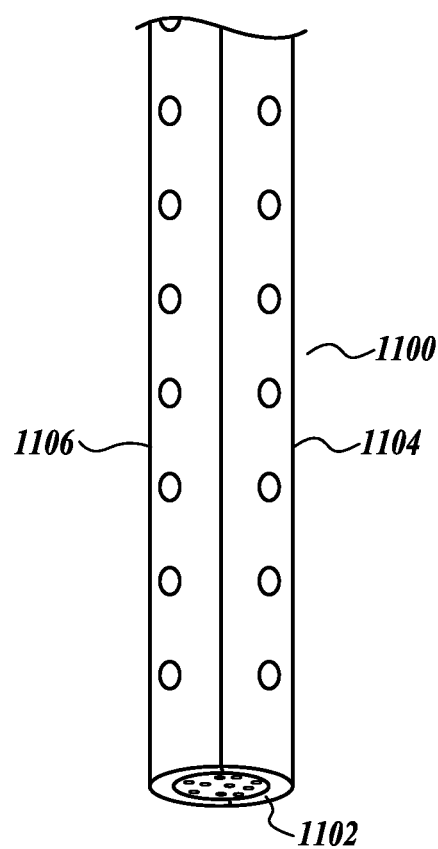
FIG. 11 is a diagrammatical illustration of a tip with LEDs of half cylinder construction for the brush and comb embodiments.

FIG. 11 illustrates a tip 1100 made from an electrically conductive first hollow half cylinder 1104 placed side-by-side to an electrically conductive second hollow half cylinder 1106, wherein first half cylinder 1104 is designated as a positive or negative terminal, and the second half cylinder 1106 is the terminal of opposite polarity as the first half cylinder 1104. An electrically insulating material or coating can be added between the first 1104 and second 1106 hollow half cylinders. In one embodiment, this allows placing one or more light-emitting diodes 1102 at the end of the tip or other locations that is powered by the two terminals by being in contact with the two terminals.

Figure 12:
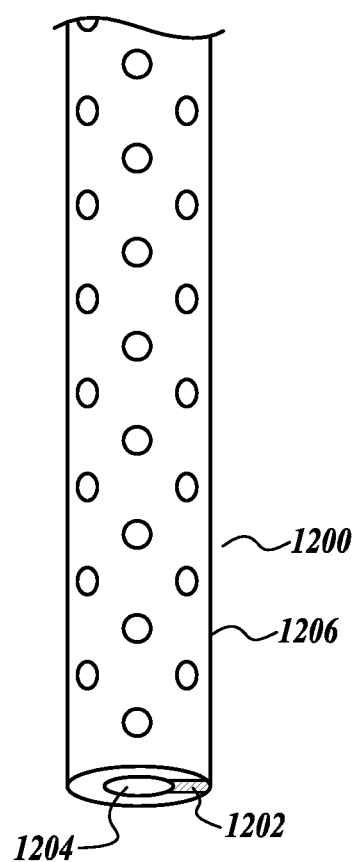
FIG. 12 is a diagrammatical illustration of a tip with LEDs of cylinder within cylinder construction for the brush and comb embodiments.

FIG. 12 illustrates a tip 1200 made from an electrically conductive first hollow inner cylinder 1204 placed inside or coaxially within an electrically conductive second hollow outer cylinder 1206, wherein first inner cylinder 1204 is a positive or negative terminal, and the second outer cylinder 1106 is the terminal of opposite polarity to the first cylinder 1204. This allows placing one or more light-emitting diodes 1202 at the end of the tip 1202 which is powered by the two terminals.

In one embodiment, depending on the power of the LEDs 1102 and 1202, thermal dissipation can be absorbed (heat-sinked) by the conductive material of the cylinders 1104, 1106, 1204, and 1206.

In one embodiment, when the LEDs 1102 and 1202 are placed at the end of the tips, the LEDs can deliver more energy to the scalp compared to being placed at the base of the tips or when the LED light is delivered through a long fiber-optic path.

In one embodiment, the LEDs 1102 and 1202 can be used for treatment, curing formula, or indicating device status (i.e., operational mode or charging status).

LEDs can be any type of a single wavelength (laser LED) or of a range of wavelengths. In one embodiment, LEDs 1102, 1202 are capable of producing light over a broad range of the electromagnetic spectrum. In one embodiment, light therapy has been used on the scalp to treat a skin condition. In one embodiment, light therapy has been used to stimulate the cells of hair follicles. The intensity of the light produced by the LEDs 1102, 1202 can be varied by controlling the current, for example.

In one embodiment, the LEDs 1102, 1202 include one or more Group III-V (GaAs) based LEDs that are capable of emitting electromagnetic radiation at wavelengths in a range spanning from green visible light to near infrared. In one embodiment, the LEDs 1102, 1202 include one or more Group III-nitride blue LED solid state emitters that are capable of emitting electromagnetic radiation at wavelengths in a range spanning from ultraviolet to blue visible light.

In one embodiment, the wavelength output of the LEDs 1102, 1202 includes one or more gallium-indium-nitrogen (GaInN) LEDs that have a wavelength output of about 360-370 nm. In other embodiments, the LEDs 1102, 1202 emit electromagnetic energy in a range of wavelengths from about 200 nm to about 2000 nm, which includes wavelengths in the ultraviolet range (about 350 nm) and near infrared (about 1200 nm).

Figure 13:
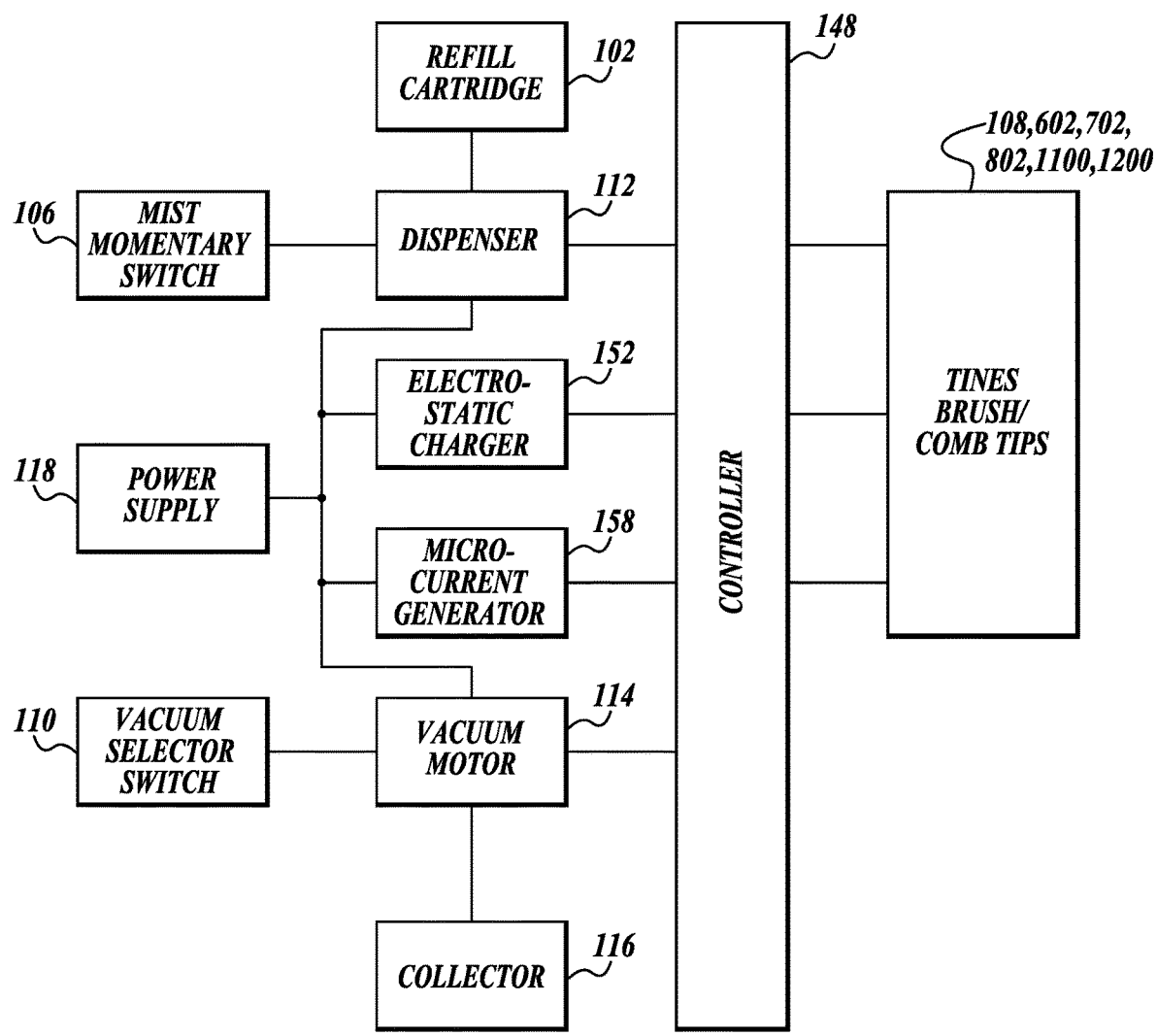
FIG. 13 is a schematic illustration showing the components of a hair and scalp treatment device.

Referring to FIG. 13, the device 100 is represented schematically to illustrate the main components.

In one embodiment, the device 100 includes a power supply 118. The device 100 can be powered by alternating current (AC) or direct current (DC). In one embodiment, the device 100 is powered through common household alternating current that relies on an electrical cord (not shown) to supply power to the device 100. In one embodiment, the device 100 is powered through direct current, such as a rechargeable battery that can be charged by plugging into a household alternating current outlet. A direct current powered device 100 allows the device to be used without staying or standing in proximity to an electrical outlet.

Figure 1:
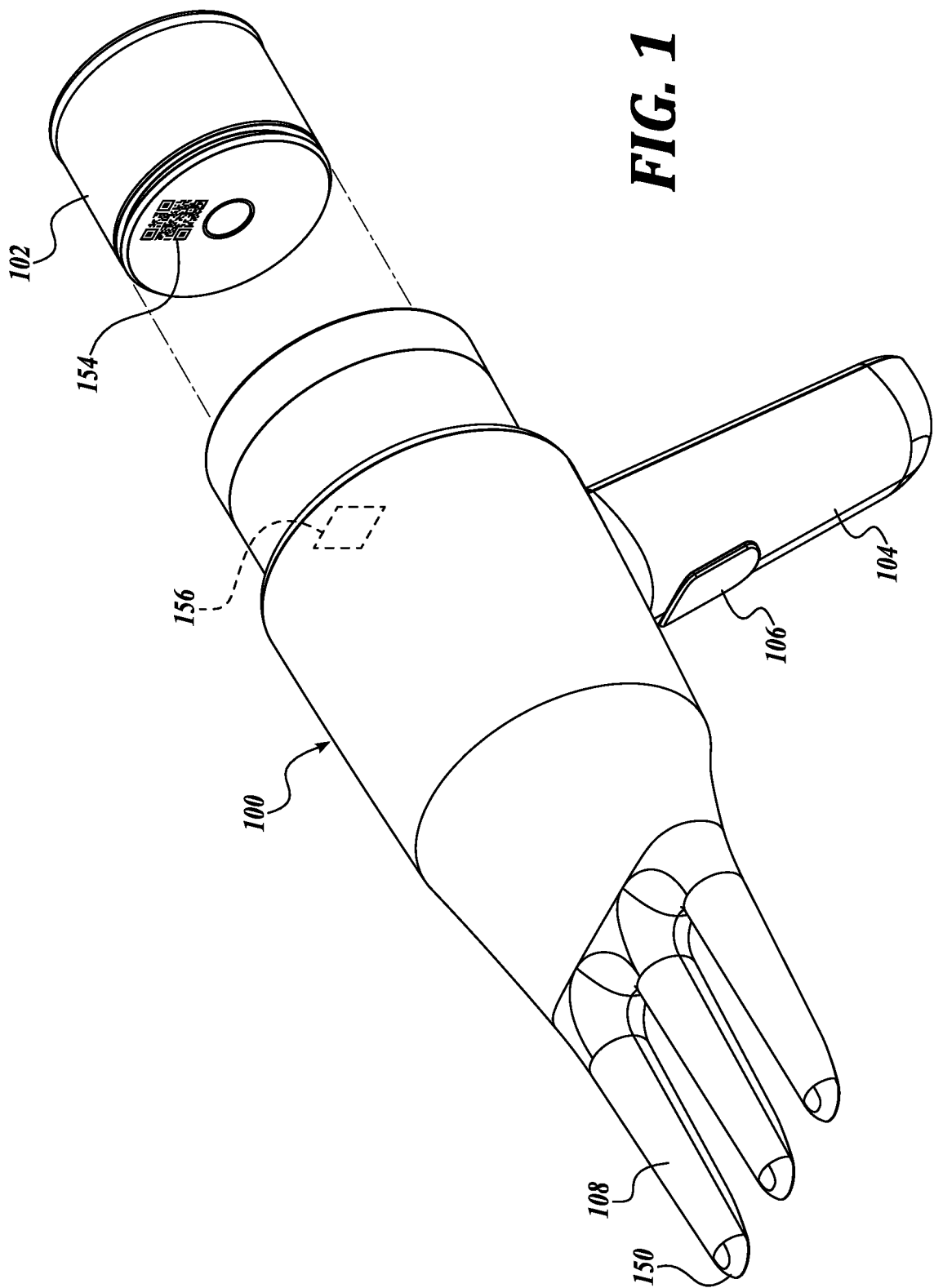
FIG. 1 is a diagrammatical illustration of a hair and scalp treatment device.

In one embodiment, the device 100 includes a formulation dispenser 112. In one embodiment, the formulation is stored in a replaceable or refillable cartridge 102. Cartridges 102 can be removable from the device 100 either to be re-filled or for disposal and replacement with a new full cartridge. Once emptied, a cartridge 102 can be replaced with a new cartridge filled with the same or different formulation or the cartridge can be refilled with the same or different formulation. As seen in FIG. 1, the cartridge 102 is inserted through the back of the device 100. The cartridge 102 is connected to supply the scalp or hair formulation to the dispenser 112. In one embodiment, the device 100 can hold multiple cartridges, wherein each cartridge is filled with a different formulation, which can be dispensed to effect different treatments and to different regions of the scalp and hair.

In one embodiment, the cartridge 102 has a product identification tag 154 (FIG. 1) that can convey instructions for operation of the device 100 based on the specific formulation contained in the cartridge 102. The device 100 may include a product identification tag reader 156 (FIG. 1) capable of reading the product identification tag 154 and processing the encoded signals into instructions for operation and control of the device based on the particular formulation. Product identification tags, include for example, bar codes, 2-D bar codes, RFID, and the like. The product identification tag is encoded with machine readable signals that convey the device settings for the particular formulation. Different formulations may have different device settings. For example, the product identification tags can include dispenser setting from liquid to fine, medium, or coarse droplets. Product identification tags can also include the dispenser pattern formation, such as flat fan versus cone, wide versus narrow, solid versus hollow, stream versus mist. Different formulations can also be used for treating different regions of the scalp and hair. Different formulations may also be used to provide different treatments to the scalp and hair. In one embodiment, the product identification tag identifies the formulation in the cartridge 102 as a containing charged particles, which controls the device 100 to turn on the electrostatic charger 152, and the product identification tag further determines the electrostatic setting, such as the particular voltage and the polarity of negative or positive.

In one embodiment, hair formulations the include cationic, anionic, or zwitterionic polymers and surfactants can be used to provide a charge to formulations that can interact with hair or scalp. In one embodiment, hair formulations can be charged with other materials, such as, chelating agents that can also function to complex molecules that impede charged interactions between charged materials and their interactions with the hair fiber to allow for more efficient charged interactions to occur.

Given that hair holds a charge (typically negative at neutral pH), this charge can be influenced by the presence of charged materials (such as the ones mentioned above) in formulation as they are applied to hair allowing for better and more efficient attraction/deposit or repulsion and aided removal.

The dispenser 112 can dispense one or more formulations through the tines 108 and tips 602, 702, 802, 1100, 1200 as a fine mist or liquid or any form in-between. In one embodiment, the dispenser 112 includes a compressor, pump, or ultrasonic wave generator to generate a mist from the formulation. In the case of a pump or compressor dispenser 112, such dispenser 112 causes air or the formulation to flow at a high velocity which propels the formulation through a fine nozzle designed for misting at the opening 130. In the case of a pump or compressor dispenser, a single dispenser 112 can be placed in the device 100. Then, the outlet of a compressor or pump dispenser 112 is routed through a system of conduits to each of the tines 108 and exits from the nozzle at the openings 130.

In an embodiment, the dispenser 112 is an ultrasonic wave nebulizer that generates a mist or vapor to dispense the formulation. This has the advantage of gentle dispersion of the formulation to reduce the amount of waste and improves control of coverage. In one embodiment, the nebulizer uses an ultrasonic wave generator that is in contact with the formulation where the frequency of the ultrasonic waves is sufficient to produce the mist. An ultrasonic wave nebulizer also includes a "mesh" nebulizer that has a vibrating mesh just touching the surface of the formulation to create the mist. Either form of ultrasonic wave nebulizer can use a piezoelectric element.

In one embodiment, the dispenser 112 operates by depressing the switch 106 (FIGS. 1 and 2). In one embodiment, the switch 106 is placed on the front side of upper part of the handle 104 to allow operation with the index finger. In one embodiment, the switch 106 is a momentary switch with the default position being the off position. A momentary switch only needs to be activated once, regardless of length of activation, to dispense a measured amount of formulation. Keeping a momentary switch 106 depressed longer does not dispense more formulation beyond the pre-measure amount. In another embodiment, the switch 106 is an on-off switch that starts and stops the dispenser 112 based on opening and closing the switch.

In one embodiment, the device 100 includes an electrostatic charger 152. An electrostatic charger can produce a positive or negative charge at a targeted area of the scalp or hair or both. The electrostatic charger 152 is connected via an electrical conductor to an electrode 150 on the end of one or more tines 108, or in the case of tips 602, 702, 802, 1100, and 1200 to one of the electrically conductive cylinders. Suitable conductive materials for the tips 602, 702, 802, 1100, and 1200 may include, for example, copper, nickel, stainless steel, aluminum, or any alloys thereof.

In one embodiment, the device 100 includes a microcurrent generator 158. A micro-current generator 158 provides a voltage across a positive terminal and a negative terminal (GND) to administer small amounts of current (micro-current) within a given range of frequencies to a region of skin or scalp. In one embodiment, the amount and frequency of electrical stimulus can be within the range of naturally-occurring electrical processes in tissues and cells. Micro-current therapy has been used to stimulate hair growth, heal injured tissues, and skin rejuvenation through stimulation of collagen and increased blood flow, for example. In one embodiment, generation of micro-currents is provided by a waveform generator. The controller 148 sends a modulated wave signal setting the amplitude, frequency, and polarity of the desired micro-current.

In one embodiment, the tips 602, 702, 802, 1100, and 1200 are connected to micro-current generator 158. The tips 602, 702, 802, 1100, and 1200 being made from conductive materials allows one of the cylinders of the tips to act as a positive terminal, which can be used to provide the microcurrents to the scalp, where the scalp acts as a ground (GND) path, which also includes the skin and tissue between the scalp and a negative terminal placed so as to be in contact with the hand, such as on the handle 104 of the device 100. In one embodiment, micro-currents can be administered between multiple tips, where one tip acts as the positive terminal and the another tip acts as the GND terminal.

In one embodiment, the tips 602, 702, 802, 1100, and 1200 being made from conductive materials also allows the tips to act as sensors. In one embodiment, one of the cylinders of each of the tips 602, 702, 802, 1100, and 1200 can act as a positive terminal, while a second cylinder of the same or different tip acts as a negative terminal. In one embodiment, impedance can be measured between any positive terminal and any negative terminal to determine scalp moisture level at a specific point or over a more general region.

In one embodiment, impedance can be measured from different tips to determine scalp moisture level across wider regions.

In one embodiment, impedance can be measured between the positive terminal or negative terminal and the scalp (via a conductive return path to handle) to determine if the tip is in contact with scalp (skin). This is useful if the application requires scalp contact; for instance, in a formula treatment and vacuuming system, where the scalp is being treated and the vacuum is at risk of vacuuming hair if the device is not operating directly on the scalp.

In one embodiment, the tips 602, 702, 802, 1100, and 1200 are connected to electrostatic charger 152. In one embodiment, the electrostatic charger 152 is used to produce a positive or a negative charge on the scalp or hair or both to attract or repel formulations to the charged areas. The tips 602, 702, 802, 1100, and 1200 being conductive allows the tips to act as electrodes. In one example, positively charged areas are created by repelling electrons from the areas, and in another example, negatively charged areas are created by attracting electrons to the areas. Electrostatic charging may be conducted by contact electrocharging, induction electrocharging, and the like.

In another example, formulations are charged while passing within the tips 602, 702, 802, 1100, and 1200. Negatively charged hair formulation droplets are attracted towards the target which can be at a lower potential.

In one embodiment, the device 100 includes a vacuum system 114 having a vacuum generating motor and collector 116. In one embodiment, a motor can be a variable speed motor. The vacuum motor 114 is connected to impeller vanes that cause a stream of air to enter through the vacuum inlet openings 132 at the tines 108, or in the case of tips 602, 702, 802, 1100, and 1200, one of the cylinders can be used for vacuum. The motor induces a stream of air to enter through the openings 132 at the tines 108, or one of the cylinders of the tips 602, 702, 802, 1100, and 1200. The stream of air can carry the used formulation along with any debris and oils washed out of the hair by the formulation, which then gets captured by a collector 116, and the air is expelled out of the device 100. In one embodiment, the collector 116 includes an annular vent placed at the back of the device 100. The vent allows the stream of air to exit the device 100, while the used and debris become trapped in the collector 116.

Figure 4:
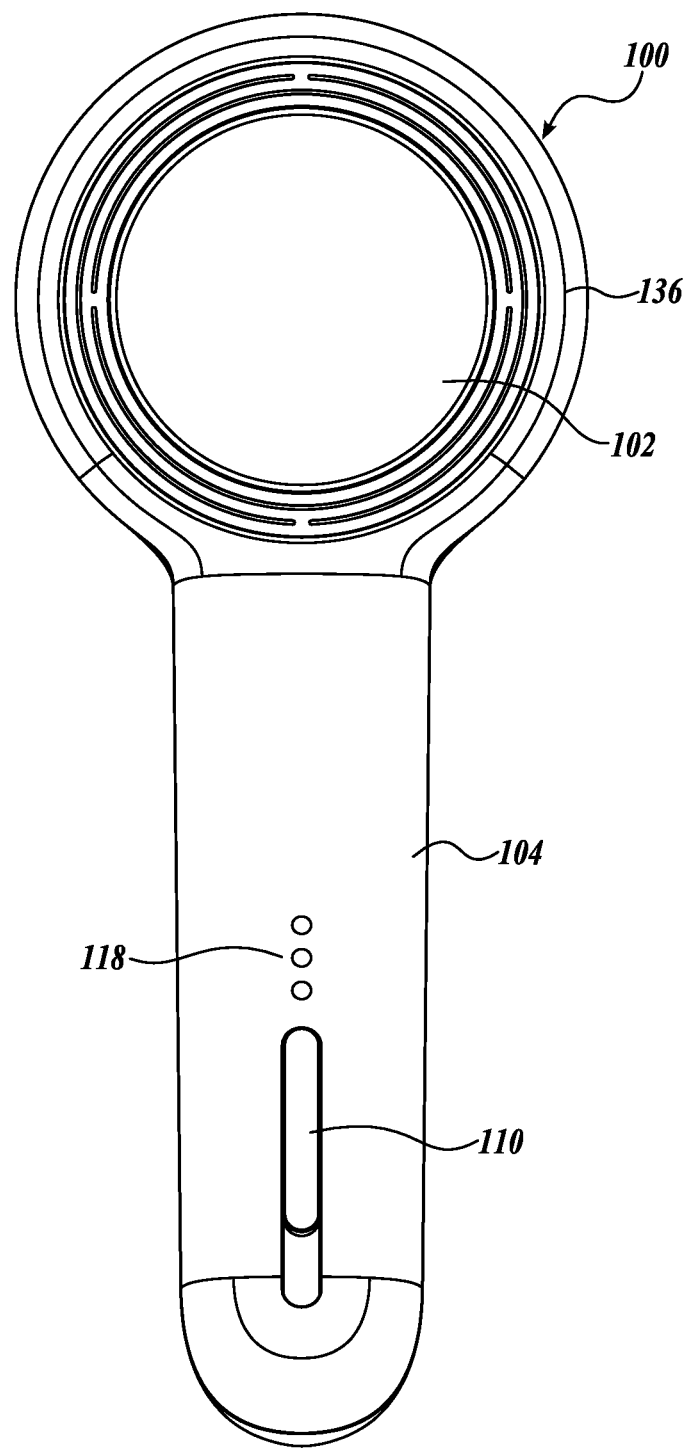
FIG. 4 is a diagrammatical illustration of a back view of the hair and scalp treatment device of FIG. 1.

In one embodiment, the vacuum motor 114 is operated by the multi-positional, multi-functional, selector switch 110 (FIG. 4). A selector switch 110 can be a slide switch or a dial switch with more than two positions, or a push button switch with more than two positions, for example. In one embodiment, a vacuum selector switch 110 includes settings for off and more than one vacuum speed setting, such as high and low. In one embodiment, the vacuum switch 110 is placed on the back side of lower part of the handle 104 to allow operation with the thumb, for example. The vacuum switch 110 can be isolated for uninterrupted vacuum. Light-emitting diodes 118 can be used to light up the selected position. The selector switch 110 remains in the selected position until moved to another position. In one embodiment, a momentary switch can replace the selector switch, wherein the default position of the momentary switch is the off position, and the momentary switch has to be depressed to start the vacuum motor. In one embodiment, the device 100 includes both a vacuum selector switch and momentary switch, wherein the momentary switch is used to operate the vacuum motor when depressed, and at the speed setting on the selector switch.

In one embodiment, the device 100 includes a controller 148. In one embodiment, the controller 148 is a digital device. The controller 148 may include one or more hardware circuits connected on a printed circuit board, or all of circuits may exist on a single chip. The controller 148 may include at least a microprocessor core and a memory. The hardware can be designed for use in small hand operated devices. The microprocessor may be implemented as multiple processors cooperatively working in parallel and series to perform instructions according to pre-programmed logic.

Instructions to control the dispenser 112, electrostatic charger 152, micro-current generator 158, and vacuum 114 can be stored in the controller memory. A memory is any type of computer-readable medium or computer storage device that can be accessed and used by one or more microprocessors to carry out the instructions. Instructions may be stored in a high-speed memory such as a EEPROM, Flash memory, RAM, or other programmable non-volatile memory.

In one embodiment, the controller 148 communicates with the dispenser 112, electrostatic charger 152, micro-current generator 158, and the vacuum 114. The controller 148 can also read the information provided on cartridges 102 to give instructions to the dispenser 112 and electrostatic charger 152 that are specific to the formulation. The controller 148 can configure one or more of the tips 602, 702, 802, 1100, and 1200 to be electrically connected to the micro-current generator 158 and electrostatic charger 152. The controller 148 can configure one or more of the tips 602, 702, 802, 1100, and 1200 to be connected to the dispenser 112 to deliver formulation in the desired form and amount. The controller can control the LEDs 1102 and 1202 to operate at the designated power and wavelength.

In one embodiment, the controller 148 can connect one or more of the tips to act as positive and negative terminals of the micro-current generator 158.

In one embodiment, the controller 148 can connect one or more of the tips to act as the electrodes for the electrostatic charger 152.

In one embodiment, the controller 148 can connect one or more of the tips to the positive terminal of the micro-current generator 158, and the scalp (skin) is part of the ground path to the negative terminal located on the device 100.

In one embodiment, the controller 148 can calculate the impedance between a positive and negative terminal of any one or more of the tips.

In one embodiment, the controller 148 uses the impedance to determine whether the tips are in contact with the scalp. In one embodiment, the controller 148 can turn off the vacuum 114 or not allow the vacuum to be turned on when it is determined that one or more tips are not in contact with the scalp.

In one embodiment, the controller 148 can use a measure of the impedance to determine the moisture of one or more regions on the scalp.

In one embodiment, the controller 148 can turn on the LEDs 1102 and 1202 based on pre-determined instructions. For example, some formulations may call for applying light in a certain wavelength. The controller 148 may be used control the LEDs 1102 and 1202 to provide a light therapy treatment. The controller 148 has instructions for determining the wavelength and power to be applied for the light therapy.

In one embodiment, the controller 148 can control the amount of formulation that is dispensed by the dispenser 112. For example, the controller 148 can turn on a pump or compressor for a predetermined amount of time that correlates to a specific amount of formulation. In one embodiment, the dispenser 112 uses a positive displacement pump, therefore, the volume displaced for each rotation of the pump can be measured with an encoder. When the rotations of the pump equal the volume of formulation to be dispensed, the controller 148 can turn off the pump.

Use of the device 100 is instinctive, the overall shape of the device 100 is familiar to users other hair appliances, such as a hair dryer, leading to simple intuitive use of the device 100. The device 100 can improve on current use of aerosol dry shampoos. The device 100 dispenses a controlled amount of formulation so that as the user combs or brushes their hair, the formulation glides onto and into the hair. The device 100 contrasts with an aerosol spray can that sprays more than is needed and produces a large cloud that covers an area well outside the user's head.

While illustrative embodiments have been illustrated and described, it will be appreciated that various changes can be made therein without departing from the spirit and scope of the invention.

The embodiments of the invention in which an exclusive property or privilege is claimed are defined as follows:

1. A device, comprising:
    a dispenser connected to a cartridge, wherein the cartridge comprises a formulation;
    a plurality of tips each having a first and second hollow chamber extending along a length of the tip, wherein the first chamber is segregated from the second chamber;
    wherein the first and second hollow chambers include a first hollow inner conductive cylinder placed inside within a second hollow outer conductive cylinder, wherein first inner cylinder is a positive or negative terminal, and the second outer cylinder is a terminal of opposite polarity to the first cylinder, and one or more light-emitting diodes extend radially from the first inner cylinder to the second outer cylinder; and
    a controller that controls the amount of formulation that is dispensed from the tips.

2. The device of claim 1, comprising a dry shampoo formulation.

3. The device of claim 1, comprising a pump which pumps the formulation to the tips.

4. The device of claim 1, comprising a nebulizer that dispenses the formulation as a mist or vapor.

5. The device of claim 1, wherein the first and second hollow chambers are made from a shape memory or piezoelectric material.

6. The device of claim 5, wherein the shape memory or piezoelectric material is selected from a polymer, ceramic, and alloy.

7. The device of claim 1, wherein the first and second hollow chambers are connected to a positive and negative terminal of a power supply.

8. The device of claim 1, wherein the first and second hollow chambers are connected to a positive and negative sensing terminal.

9. The device of claim 1, wherein the controller calculates an impedance between the positive terminal and the negative terminal.

10. The device of claim 9, wherein the controller calculates a moisture level based on the impedance.

11. The device of claim 9, wherein the controller determines contact between the terminals and skin based on the impedance.

12. The device of claim 1, wherein one of the first or the second hollow chambers is connected to a vacuum.

13. The device of claim 1, wherein the first hollow chamber has first openings along a length of the first hollow chamber leading from within the first hollow chamber to the exterior, and the second hollow chamber has second openings along a length of the second hollow chamber leading from within the second hollow chamber to the exterior.

14. The device of claim 1, wherein the first and second hollow chambers have openings at the ends of the chambers.

15. The device of claim 1, comprising a body structure having a handle connected at an obtuse angle to a central portion of the body structure, the handle makes the obtuse angle with respect to a front end of the body structure, wherein the tips are located at a front end of the body structure.

* * * * *